US011344442B1

(12) United States Patent
McVeigh et al.

(10) Patent No.: US 11,344,442 B1
(45) Date of Patent: May 31, 2022

(54) ANKLE BRACE

(71) Applicants: Jason McVeigh, Knoxville, TN (US); Russell Betcher, Knoxville, TN (US)

(72) Inventors: Jason McVeigh, Knoxville, TN (US); Russell Betcher, Knoxville, TN (US)

(*) Notice: Subject to any disclaimer, the term of this patent is extended or adjusted under 35 U.S.C. 154(b) by 344 days.

(21) Appl. No.: 16/436,902

(22) Filed: Jun. 10, 2019

(51) Int. Cl.
*A61F 5/01* (2006.01)
*A61F 13/06* (2006.01)

(52) U.S. Cl.
CPC .......... *A61F 5/0111* (2013.01); *A61F 13/066* (2013.01); *A61F 2005/0167* (2013.01); *A61F 2005/0181* (2013.01)

(58) Field of Classification Search
CPC .... A61F 5/0111; A61F 5/0113; A61F 5/0127; A61F 5/05841; A61F 5/0585; A61F 13/06; A61F 13/064; A61F 13/066; A61F 13/0273; A61F 2005/0167; A61F 2005/0181; A43B 7/14; A43B 7/18; A43B 7/20; A43B 3/122; A43B 3/126; A43B 3/16; A43B 3/163; A43B 3/18; A43B 3/20; A43B 3/22; A43B 5/12; A63B 71/1225; A63B 2071/1275; A43C 11/1493
See application file for complete search history.

(56) References Cited

U.S. PATENT DOCUMENTS

| | | | |
|---|---|---|---|
| 5,067,486 A * | 11/1991 | Hely | A61F 13/066 602/27 |
| 8,865,962 B2 * | 10/2014 | Weidemann-Hendrickson | A61F 13/64 602/53 |
| 9,393,146 B2 * | 7/2016 | Gaylord | A61F 5/0111 |
| 2015/0313743 A1 * | 11/2015 | Ostergard | A61F 5/0111 602/27 |

* cited by examiner

*Primary Examiner* — Keri J Nelson
(74) *Attorney, Agent, or Firm* — Esther L. Roberts; Tom Kulaga

(57) ABSTRACT

The present general inventive concept, in various embodiments, includes a brace for protective or therapeutic restraint of the ankle and/or foot. In some embodiments, the brace comprises a holding pocket of flexible material for stabilizing the ankle or foot, a means for releasably and adjustably attaching the holding pocket around the foot and ankle, a first support strap including a means for releasably and adjustably binding the first support strap to itself, a first support cuff including a means for releasably and adjustably tightening the first support cuff upon itself, a second support strap including a means for releasably and adjustably binding the second support strap to itself, and a second support cuff including a means for releasably and adjustably tightening the second support cuff upon itself.

16 Claims, 13 Drawing Sheets

ANKLE BRACE

CROSS-REFERENCE TO RELATED APPLICATIONS

Not Applicable.

STATEMENT REGARDING FEDERALLY-SPONSORED RESEARCH OR DEVELOPMENT

Not Applicable.

BACKGROUND OF THE INVENTION

The present general inventive concept relates generally to an ankle brace, and more specifically, a brace for protective or therapeutic restraint of the ankle or foot.

BRIEF SUMMARY

The present general inventive concept, in various embodiments, includes a brace for protective or therapeutic restraint of the ankle and/or foot. In some embodiments, the brace comprises a holding pocket for stabilizing the ankle or foot, the holding pocket being made from flexible material, the holding pocket also including a bottom having an interior surface and an exterior surface, a back having an interior surface and an exterior surface, a right side having an interior surface and an exterior surface, and a left side having an interior surface and an exterior surface, said bottom and said back being permanently affixed to said right side and said left side to form said holding pocket, a means for releasably and adjustably attaching the right side to the left side to secure the holding pocket around the foot and ankle, a first support strap having an interior surface, an exterior surface and two opposing ends, the interior surface of the first support strap being permanently affixed to the exterior surface of the back of the holding pocket, a means for releasably binding the two ends of the first support strap, a first support cuff having an interior surface and an exterior surface, the interior surface of the first support cuff being permanently affixed to the exterior surface of the first support strap so as to layer the first support cuff onto the first support strap on the back of the holding pocket, a means for releasably closing the first support cuff to releasably and adjustably tighten it upon itself, a second support strap having an interior surface, an exterior surface and two opposing ends, the interior surface of the second support strap being affixed to the exterior surface of the first support cuff, and a means for releasably binding the two ends of the second support strap, and a second support cuff having an interior surface and an exterior surface, the interior surface of the second support cuff being affixed to the exterior surface of the second support strap so as to layer the second support cuff onto the second support strap on the back of the holding pocket, and a means for releasably closing the support cuff to releasably and adjustably tighten it upon itself.

Some embodiments include a front panel or tongue. In some embodiments that include the front panel, the front panel can be affixed to the right side of the holding pocket, or the left side of the holding pocket, or to both the right and left side of the holding pocket. Typically, when the front panel is included in an embodiment, the means to releasably affix the right and left sides of the holding pocket are structured so as to also encompass the front panel and secure it against the front of the ankle. Some examples of the means to releasably affix the right side of the holding pocket to the left side of the holding pocket include, but are not limited to, hook and loop, buttons, snaps, zippers, rivets, screws, grommets, eyelets and laces and the like, or any combination thereof. Some embodiments include an opening at the juncture of the distal end of the back and the posterior end of the bottom of the holding pocket that allows the heel of a user's foot to be exposed. In some exemplary embodiments, the brace is constructed of thin, flexible material, such as, but not limited to, ballistic nylon, waterproof breathable fabric, mesh knit, or other lightweight, flexible materials. In some embodiments, hook and loop closure material is utilized on the first and second support cuffs to releasably affix each cuff to itself for closure to provide adjustable support around the ankle. In some embodiments, the support cuff material is elasticized. In some embodiments, hook and loop closure material is utilized on the opposing ends of the first support strap. In some embodiments, hook and loop closure material is utilized on the opposing ends of the second support strap. In some exemplary embodiments, hook and loop closure material is utilized on the opposing ends of the first support strap, the first support cuff, the second support strap, and the second support cuff to provide for maximum adjustability, especially under performance stress conditions, such as, for one example, when the wearer continues to utilize the ankle and foot in elite sports activities. In some embodiments, the exterior surface of the second support strap is permanently affixed to the interior surface of the second support cuff while the interior surface of the second support strap is removeably affixed to the exterior surface of the first support cuff so as to facilitate separate use or installation of the second support strap and second support cuff; in exemplary such embodiments, the exterior surface of the first support cuff includes a removeably affixable surface such as, but not limited to, hook and loop closure material, to secure the second support strap and second support cuff to the first support cuff, and the interior surface of the second support cuff includes a removeably affixable surface, such as, but not limited to, hook and loop closure material, to aid in securing the second support strap and second support cuff to the first support cuff. In some exemplary embodiments, the second support strap include a mark, such as for example, but not limited to, a shoe logo, sponsor logo, trademark, brand, sports team logo, or similar ornamental feature.

The present general inventive concept can provide, inter alia, preventative or therapeutic restraint of the normal movements of the ankle and/or foot. This includes, but is not limited to, inversion or eversion relative to the lower leg in excess of the natural limits of movement typically available to the ankle and/or foot. Typically, either to restrict an injured ankle/foot or to restrict a healthy ankle/foot to lower the risk of injury, an ankle brace should be used regularly. Ease of application, speed of application, and ease and speed of removal are vital components of an ankle brace with high utility.

Typically, any support or restriction placed outside the shoe is provided via disposable adhesive material, commonly called athletic tape or "spat tape." Spat tape, being a disposable adhesive material, is limited to a single use; it is not reusable. Further, spat tape must be removed either by unwinding or cutting it off, which delays access to the ankle or foot in the event of injury and may caused an injured person to experience increased pain or discomfort due to motion during the removal process as the tape is unwound or cut off. Further, tape may not allow for the adjustability provided by the present general inventive concept. Also, tape may not provide for the quality of joint restriction provided by the present general inventive concept. The present general inventive concept provides for repeated outside the shoe or over-the-shoe uses and also provides for rapid removal and access to the underlying ankle and foot, should the need arise. Further, the present general inventive concept provides for optimal adjustability and restriction of the joint, by providing a second support strap and a second support cuff, independent of the first support strap and first cuff. In various embodiments, the second support strap—being outside the footwear—includes space for logos, images, or other text or symbols, for whatever use the wearer deems appropriate.

BRIEF DESCRIPTION OF THE DRAWINGS

A wide variety of potential embodiments will become more clearly understood from the following detailed description of certain exemplary embodiments, read together with the accompanying drawings in which:

FIG. 1b is a diagram illustrating a partial rear view of the embodiment of the ankle brace shown in FIG. 1a.

DETAILED DESCRIPTION OF THE INVENTION

The following detailed description may recite various descriptive terms such as horizontal, vertical, top, bottom, upward, downward, left, right, etc., when referring to the figures, but the present general inventive concept is not limited to any such terms or physical orientations. Such terms are used for convenience of description only, and could be reversed, modified, or interchanged without departing from the broader scope and spirit of the present general inventive concept.

Figure 1A:
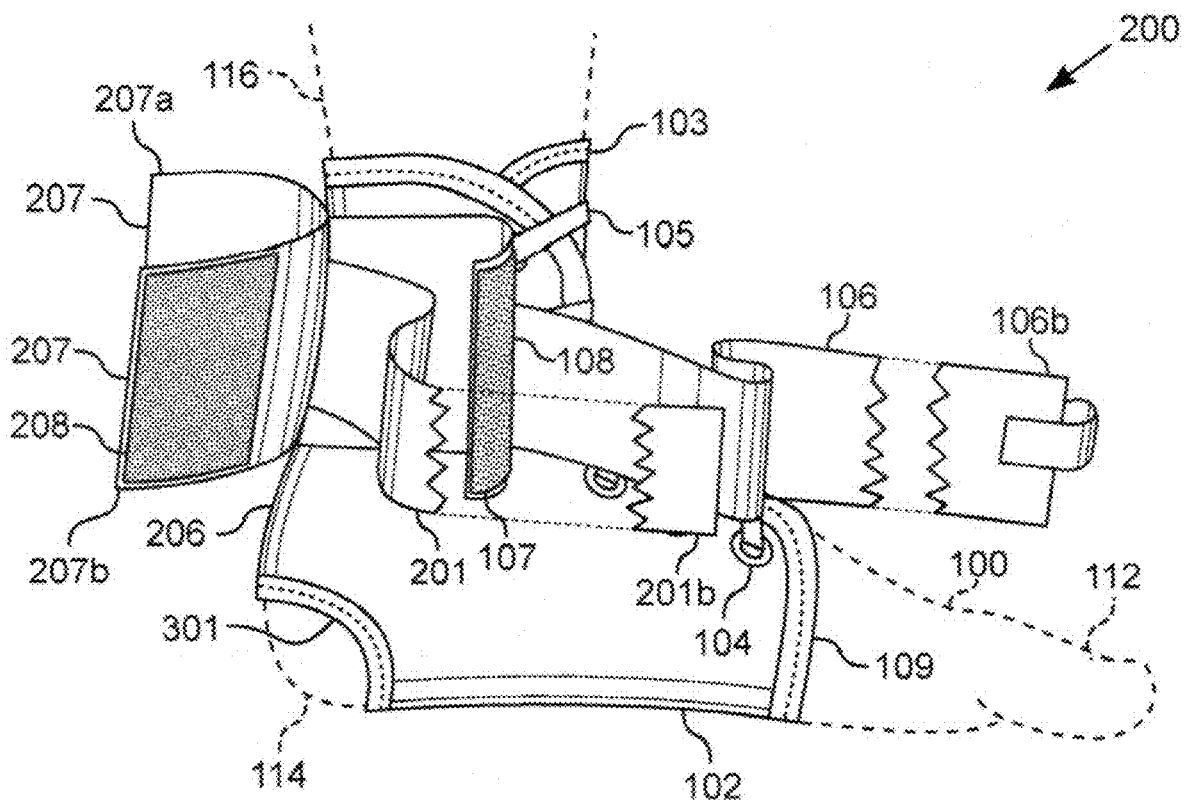
FIG. 1a is a diagram illustrating a top view of one embodiment of the ankle brace.
Figure 1B:
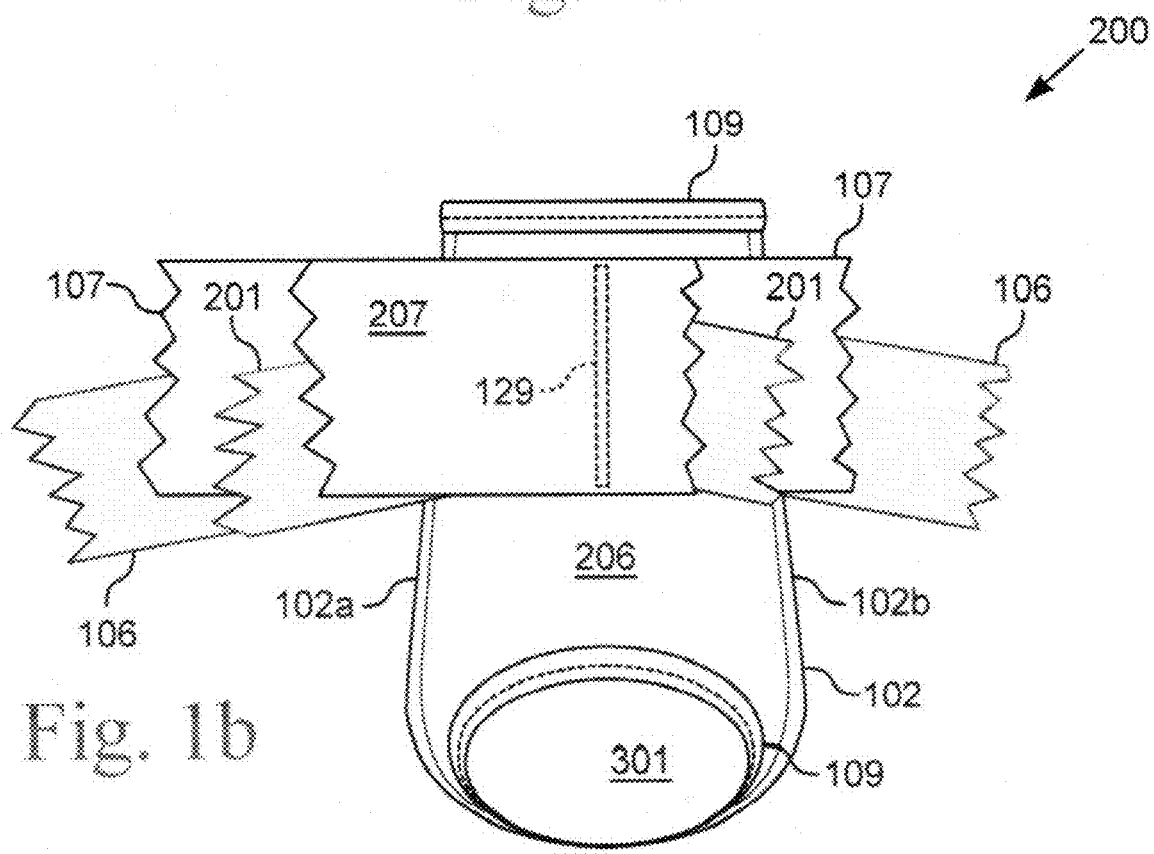

FIG. 1a illustrates a top view of one embodiment of the ankle brace 200. FIG. 1b illustrates a partial rear view of the ankle brace 200 shown in FIG. 1a. The ankle brace 200 includes a holding pocket 102, a first support strap 106, a first support cuff 107, a second support strap 201, and a second support cuff 207. The various straps 106, 201 and cuffs 107, 207 include various connectors, such as hook and loop closure material, that are shown in detail in various other figures.

The holding pocket 102 wraps around the foot 100 and ankle 116. The pocket 102 is a thin, flexible material, such as, but not limited to, ballistic nylon, waterproof breathable fabric, mesh knit, or other lightweight, flexible materials. The pocket 102 includes a front, or tongue, 103 and a set of grommets 104 through which a lace 105 is threaded to secure the pocket to the foot 100 and ankle 116. In various embodiments, the tongue 103 is attached to one side 102a, 102b or both sides 102a, 102b or is omitted entirely. In another embodiment, the holding pocket 102 is a sleeve that fits over a portion of the ankle 116 and foot 100. The purpose of the pocket 102 is to support the various straps 106, 201 and cuffs 107, 207 at a specific position on the foot 100.

In the illustrated embodiment, the edges of the pocket 102 have edging 109 that prevents the edges of the fabric from rolling and fraying. The pocket 102 has a left side 102a and a right side 102b. The front portion of the pocket 102 is open with the person's forefoot and toes 112 extending from the opening. The pocket 102 has a back 206. In the illustrated embodiment, the pocket 102 is a sheet of fabric with one or more layers. In the illustrated embodiment, there is an opening 301 to accommodate the heel 114 of the foot 100.

Figure 3:
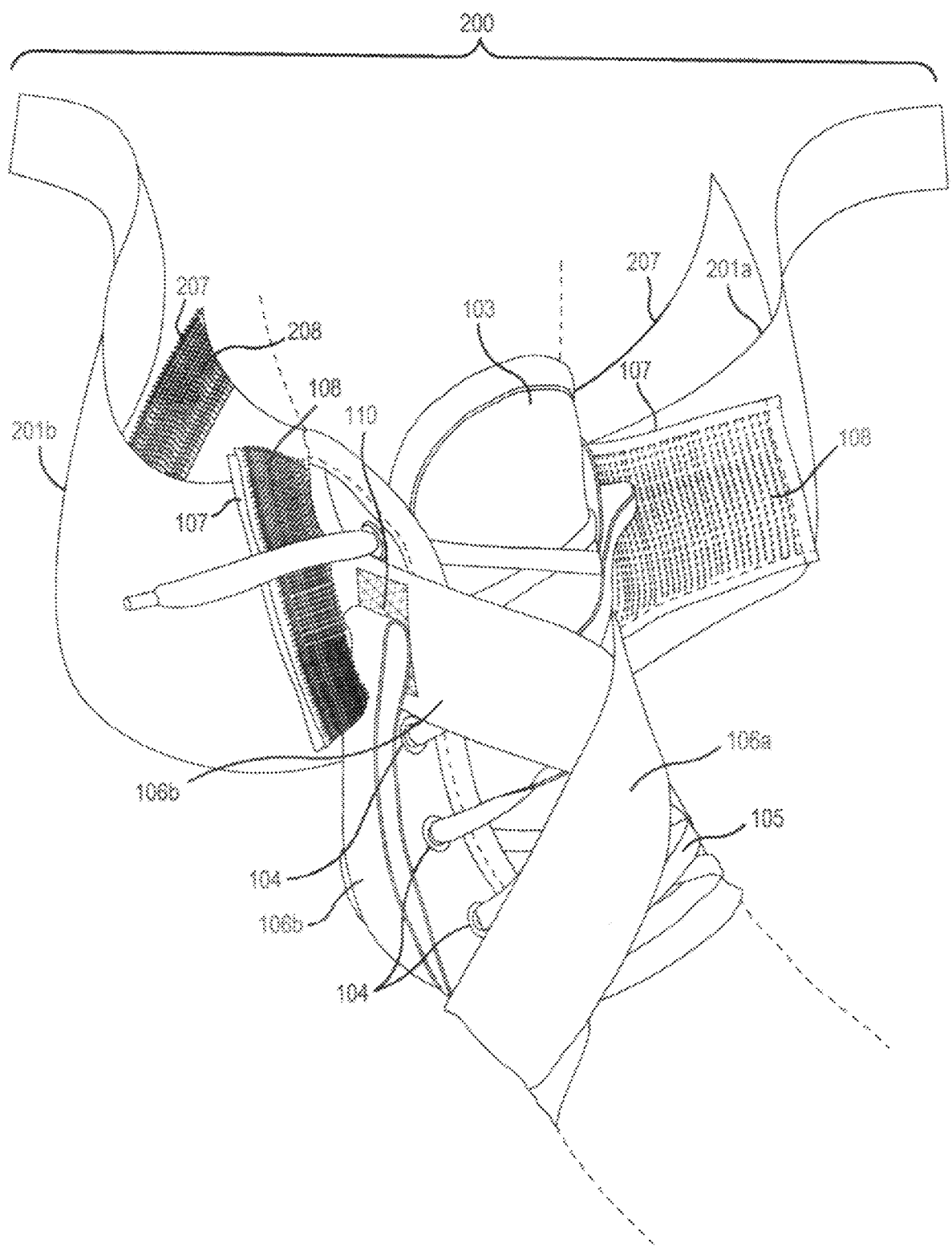
FIG. 3 is a diagram illustrating one embodiment of an ankle brace with the first support strap in place.

The first support strap 106 is attached to the back 206 at a medial section of the strap 106. In another embodiment, the first strap 106 has two pieces or sections that are joined at the back 206 to form a long strap. The first support strap 106 is webbing that has sufficient length to wrap around the pocket 102 while being worn, such as illustrated in FIG. 3. In one embodiment, the first strap 106 is non-stretchable. In another embodiment, the strap is either stretchable or elastic. The illustrated embodiment shows the first support strap 106 attached such the strap 106 extends downward with the distal ends lower than the attachment point at the back 206 of the pocket 102. The downward angle of the first support strap 106 ensures that the strap 106a, 106b does not buckle or wrinkle when the strap 106a, 106b is wrapped around the pocket 102 with the foot 100 inside the pocket 102. The distal ends of the first support straps 106a, 106b each have a pull tab 215a, 215b. The pull tabs 215a, 215b permit the respective one of the first support straps 106a, 106b to be pulled taut when wrapped around the pocket 102.

Figure 5:
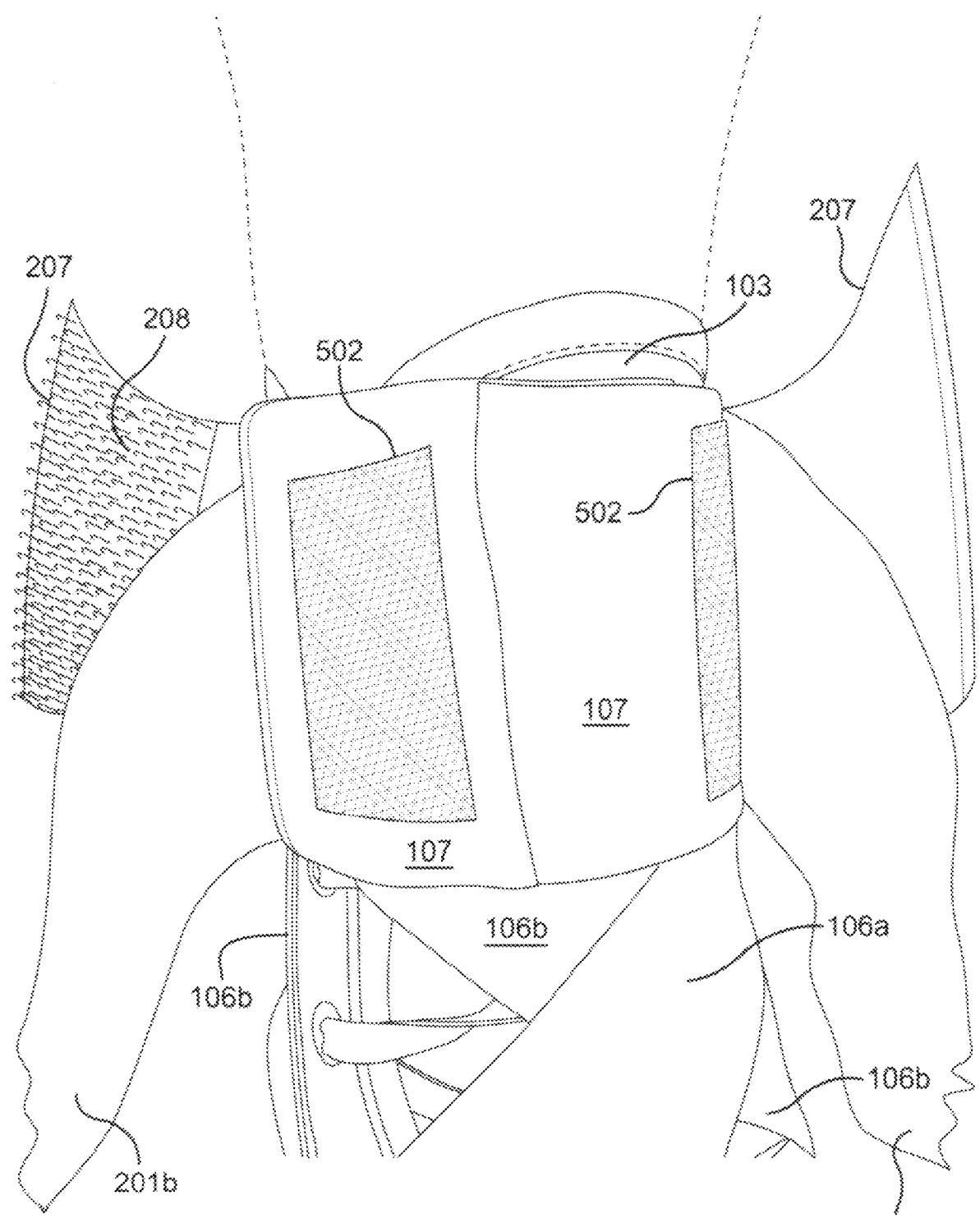
FIG. 5 is a diagram illustrating one embodiment of an ankle brace with the first support strap in place, the first support cuff in place, and the second support strap and the second support cuff ready to place.
Figure 6:
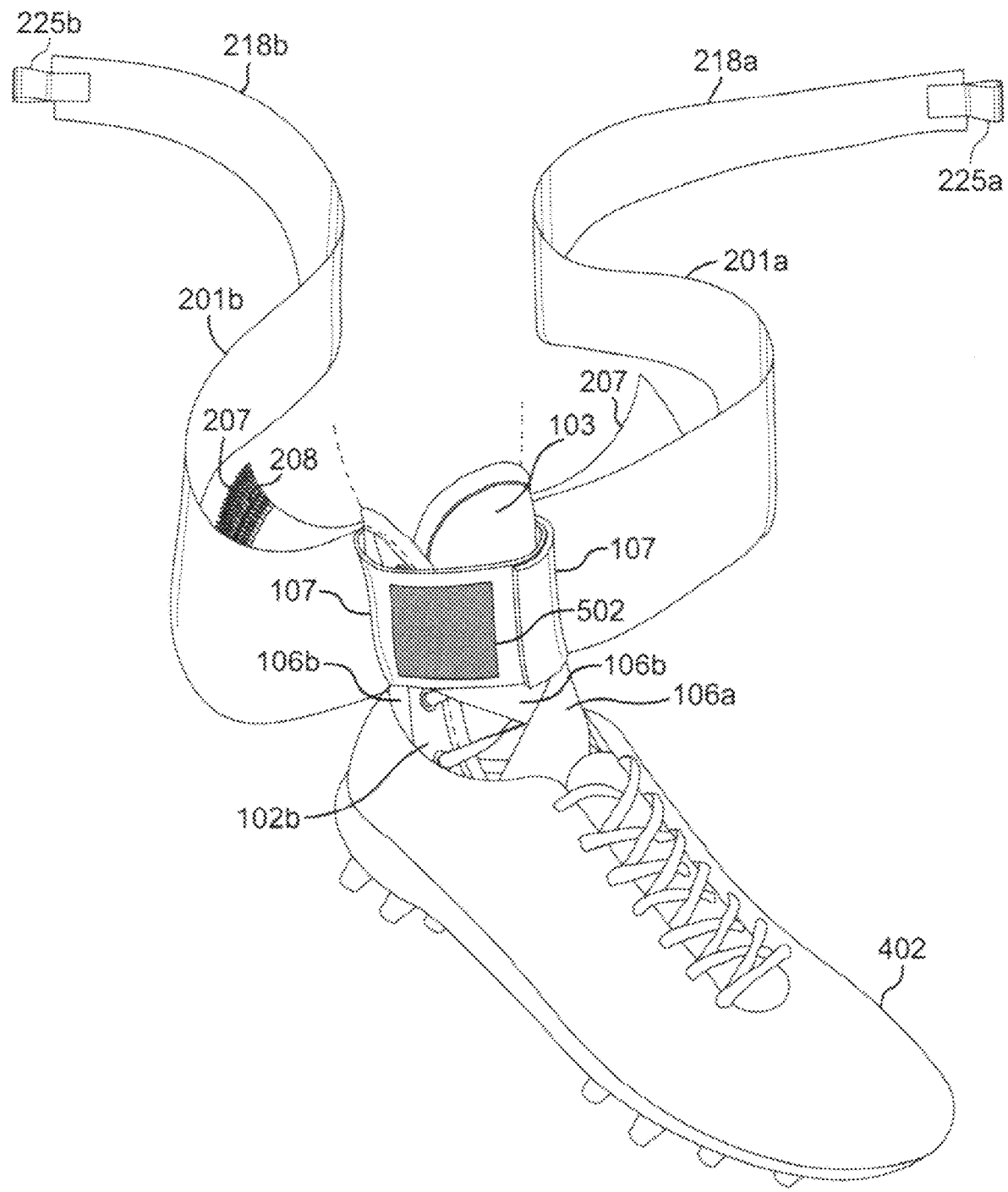
FIG. 6 is a diagram illustrating one embodiment of an ankle brace with the first support strap in place, the first support cuff in place, and the second support strap and the second support cuff ready to place.

The first support cuff 107 is attached to the back 206 at a medial section of the cuff 107. The first strap 106 is positioned between the first cuff 107 and the back 206 of the pocket 102. The first cuff 107 has a length sufficient to wrap around the ankle 116 with the ends of the cuff 107 overlapping, such as illustrated in FIGS. 5 & 6. The cuff 107 is webbing that is stretchable. In another embodiment, the first cuff 107 is a non-stretchable material. Each end of the first cuff 107 includes a fastener 108 on opposite surfaces of the first cuff 107 such that the ends of the cuff 107 are releasably attachable, one end to the other, when the cuff ends overlap. In one embodiment, the fastener 108 is one-half of a hook-and-loop fastening system. In another embodiment, the fastener 108 is a material that releasably adheres to the first strap 106, the pocket 102, and the outer surface of the first cuff 107.

The second support strap 201 is attached to the back 206 at a medial section of the second strap 201. In another embodiment, the second strap 201 has two pieces or sections that are joined at the back 206 to form a long strap. The second support strap 201 is attached to the first support cuff 107 at the back 206. In another embodiment, second support strap 201 remains unattached from the first support cuff 107 and is separate from the back 206. The second support strap 201 is webbing that has sufficient length to wrap around the shoe 402 while the pocket 102 is being worn inside the shoe, such as illustrated in FIGS. 8 to 11. In one embodiment, the second strap 201 is non-stretchable. In various such embodiments the second strap 201 is two-ply or double-faced with the inner face tacky or non-slip and the outer face wear resistant. In this way second support strap 201 functions similarly to spat tape when the strap 201 is wrapped around a shoe 402. In another embodiment, the strap is stretchable. The downward angle of the second support strap 201 ensures that the strap 201a, 201b does not buckle or wrinkle when the strap 201a, 201b is wrapped around the shoe 402 when the pocket 102 with the foot 100 is inside the shoe 402. The second support strap 201 has a width that is the same as or slightly wider than the first support strap 106. In one embodiment, the distal ends of the second support straps 201a, 201b each have a pull tab 225a, 225b. The pull tabs 225a, 225b permit the respective one of the second support straps 201a, 201b to be pulled taut when wrapped around the shoe 402.

Figure 9:
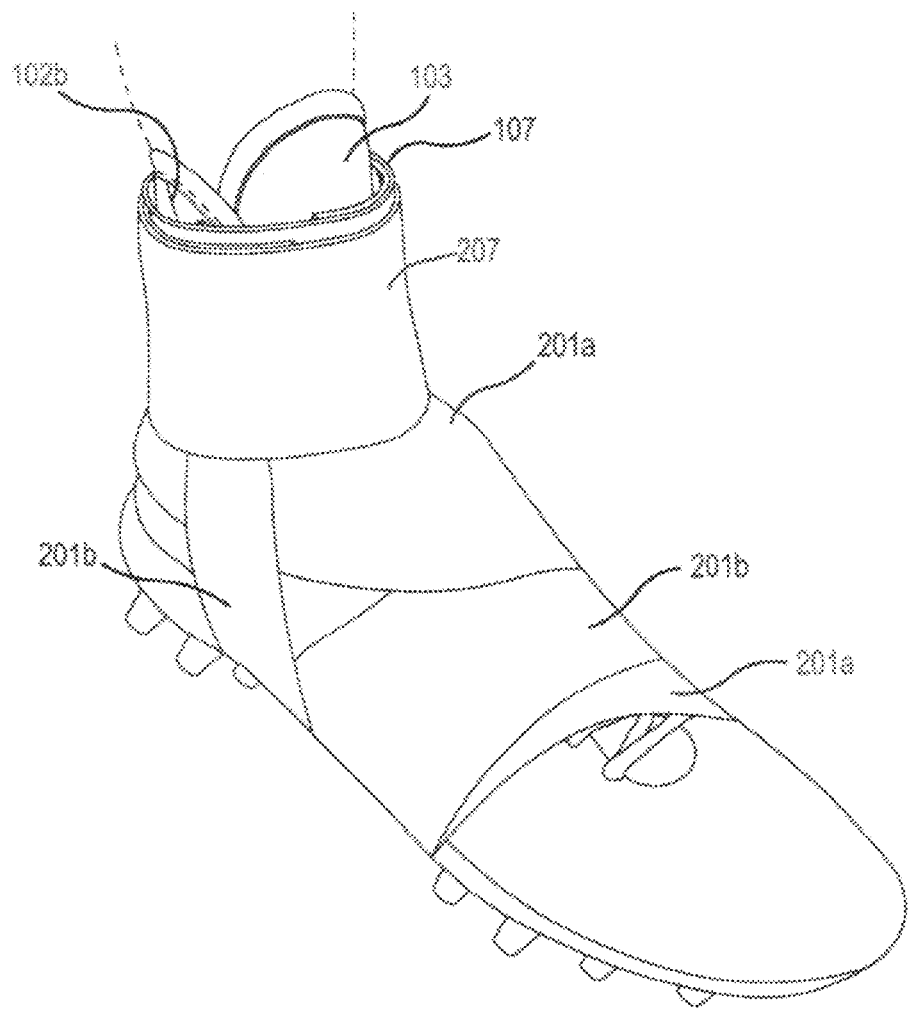
FIG. 9 is a diagram illustrating one embodiment of an ankle brace with the second support strap in place and the second support cuff in place.
Figure 10:
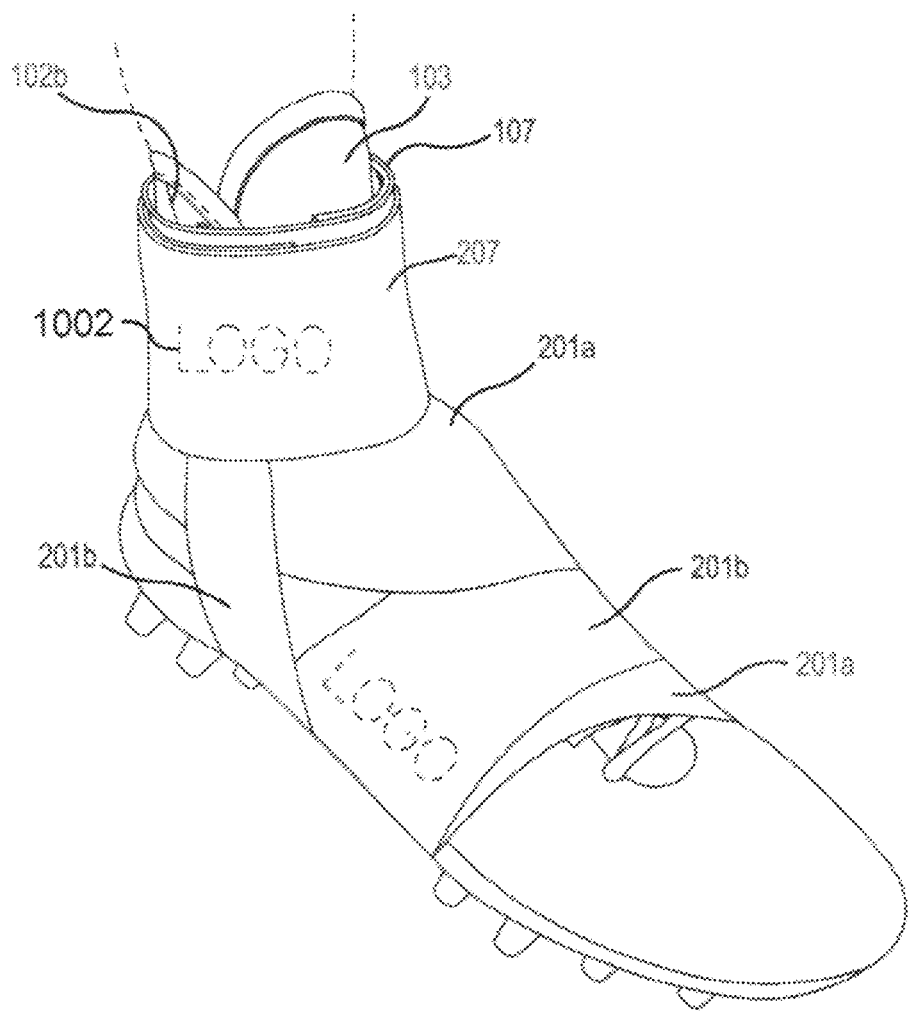
FIG. 10 is a diagram illustrating one embodiment of an ankle brace with logo placement on the second support strap.
Figure 11:
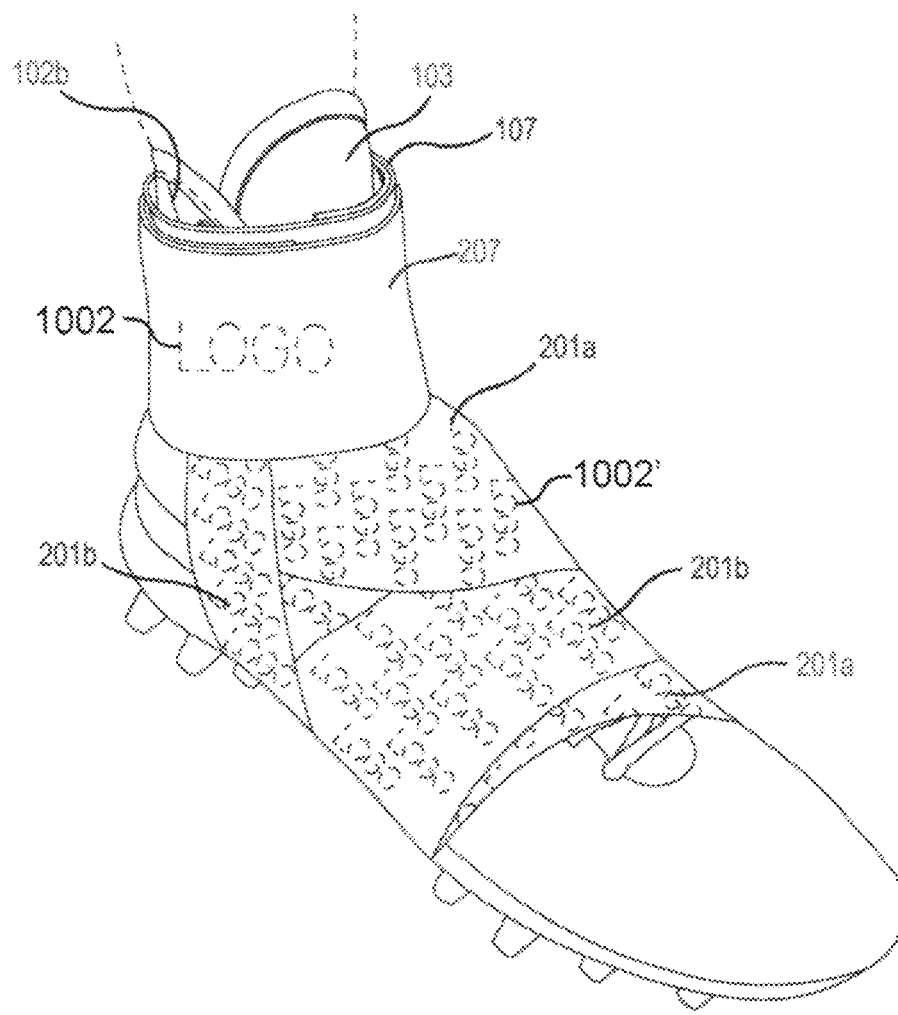
FIG. 11 is a diagram illustrating one embodiment of an ankle brace with one embodiment of an ankle brace with the logo placement on the second support strap.

The second support cuff 207 is attached to the back 206 at a medial section of the cuff 207. The second support cuff 207 is positioned outside the second support strap 201 at the back 206 of the pocket 102. In another embodiment, the second support cuff 207 remains unattached from the back 206 and second support strap 201 is attached to second support cuff 207 at a medial section of the cuff 207 and the support strap 201, with second support cuff 207 being removably affixable to first support cuff 107 to facilitate separate application of the second support cuff 207 and second support strap 201. The second support cuff 207 has a length sufficient to wrap around the ankle 116 with the ends 207a, 207b of the cuff 207 overlapping, such as illustrated in FIGS. 9 to 11. The second cuff 207 is webbing that is stretchable or elastic. In another embodiment, the second cuff 207 is a stiff webbing that forms a rigid, substantially cylindrical shaped configuration when wrapped around the ankle 116. Each end 207a, 207b of the second cuff 207 includes a fastener 208 on the surface of the second cuff 207 such that the ends of the cuff 207 are releasably attachable. In one embodiment, the fastener 208 is one-half of a hook-and-loop fastening system. In another embodiment, the fastener 208 is a material that releasably adheres to the second strap 201, the first cuff 107, and the outer surface of the second cuff 207.

In the illustrated embodiment, the first cuff 107 and the second cuff 207 have a width greater than the width of the first strap 106 and the second strap 201. The second strap 201 and second cuff 208 are positioned on the back 206 so that the cuff 207, when wrapped around the ankle 116, has a bottom edge that is proximate the top of the shoe 402 and the cuff 207 has a top edge that is above the talus between the ankle 116 and the foot 100.

In one embodiment, the pocket 102, straps 106, 201, and cuffs 107, 207 are secured together by a seam 129 sewn through the first strap 106, the first cuff 107, the second strap 201, the second cuff 207, and the back 206 of the pocket 102. In other embodiments the various straps 106, 201 and cuffs 107, 207 are secured to the back 206 with rivets or other fasteners.

Figure 2:
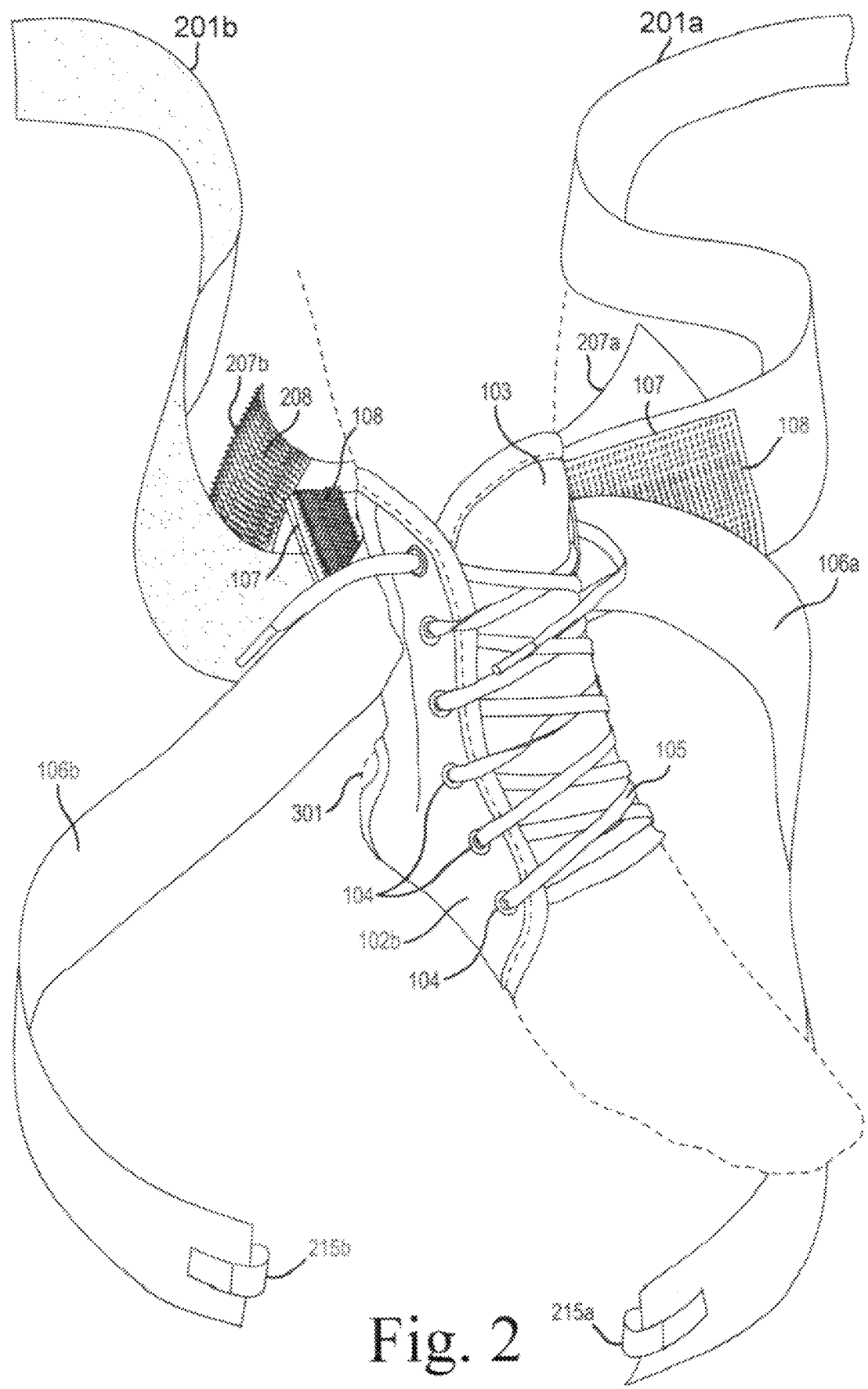
FIG. 2 is a diagram illustrating an isometric view of one embodiment of an ankle brace showing the right side and top, with the straps hanging free.

FIG. 2 illustrates a side elevational view of the ankle brace 200. As shown in FIG. 2, the holding pocket 102 includes right side 102b, left side 102a, back 206, front 103, and, in this embodiment, opening 301 for allowing the heel of the foot to be exposed. Holding pocket 102 is shown in its deployed configuration, and the straps 106, 201 and cuffs 107, 207 are shown in their non-deployed configuration. Holding pocket 102 is tightened around the foot by releasably affixing right side 102b to left side 102a. In the illustrated embodiment, the right side 102b is releasably affixed to the left side 102a by the holes 104 laced through with the lace 105. First support strap 106, having opposing ends 106a and 106b, also shown in FIG. 2, is, in the illustrated embodiment, one long continuous whole, affixed at the midpoint to the back 206 of holding pocket 102 by affixing the interior surface of the midpoint of first support strap 106 to the exterior surface of back 206. In some embodiments, means for releasably affixing first support strap opposing end 106a to holding pocket 102 include hook and loop closure material. Similarly, in some embodiments, means for releasably affixing first support strap opposing end 106b to holding pocket 102 include hook and loop closure material. In some embodiments, pull tabs 215a and 215b are included on opposing ends 106a and 106 b, respectively, to maximize efficiency when placing or removing first support strap 106. Further illustrated in FIG. 2 is a first support cuff 107; typically, the means to secure support cuff 107 to itself is hook and loop material 108. If hook material 108 is affixed on one end of the interior surface of first support cuff 107, loop material (not shown) would be affixed on the exterior surface of the other end of first support cuff 107. First support cuff 107, in the illustrated embodiment, is affixed to the back 206 of holding pocket 102 by attaching the interior surface of first support cuff 107 to the exterior surface of first support strap 106.

As further illustrated in FIG. 2, second support strap 201, having opposing ends 201a and 201b, is, in the illustrated embodiment, one long continuous whole, affixed at the midpoint to the back 206 of holding pocket 102 by affixing the interior surface of the midpoint of second support strap 201 to the exterior surface of back 206. In some embodiments, means for releasably affixing second support strap opposing end 201a to holding pocket 102 include hook and loop closure material. Similarly, in some embodiments, means for releasably affixing second support strap opposing end 201b to holding pocket 102 include hook and loop closure material. In some embodiments, the interior surface of second support strap 201 is comprised of a material having a tacky or gripping surface, to facilitate partial grip around the shoe 402 to maintain the most positive placement of second support strap 201. Further illustrated in FIG. 2 is second support cuff 207; typically, the means to secure support cuff 207 to itself include hook and loop material 208. If hook material 208 is affixed on one end of the interior surface of second support cuff 207, loop material (not shown) would be affixed on the exterior surface of the other end of second support cuff 207. Second support cuff 207, in the illustrated embodiment, is affixed to the back 206 of holding pocket 102 by attaching the interior surface of second support cuff 207 to the exterior surface of first support strap 106.

FIG. 3 illustrates an exemplary embodiment of the ankle brace 200, illustrating the first support strap 106 in place. As shown in FIG. 3, in some embodiments, brace 200 is secured around the wearer's foot via multiples of hole 104 set in rows within right side 102b and mirrored within left side 102a, each of hole 104 being releasably laced together via lace 105 in various lacing patterns.

Once holding pocket 102 is secured around the ankle 116, such as by lace 105 releasably tightened through holes 104, first support strap 106 is wrapped so that opposing end 106a crosses in a diagonal pattern over the top of the foot and under the bottom of the foot, then opposing end 106a is releasably secured against itself on the left side 102a of holding pocket 102 by engaging the first strap connector 110. Similarly, first support strap's opposing end 106b crosses in a diagonal pattern over the top of the foot and under the bottom of the foot, then opposing end 106b is releasably secured against itself on the right side 102b of holding pocket 102 by engaging the corresponding first strap connector 110. In various embodiments, first support strap opposing ends 106a and 106b are of sufficient length to extend vertically upwards to underlie first support cuff 107 and releasably adhere to tacky material 502 for temporarily securing opposing end 106a to itself and opposing end 106b to itself. Once first support strap 106 has been secured, first support cuff 107 is releasably secured upon itself. In some embodiments, hook and loop material 108 is utilized to close first support cuff 107.

Figure 4:
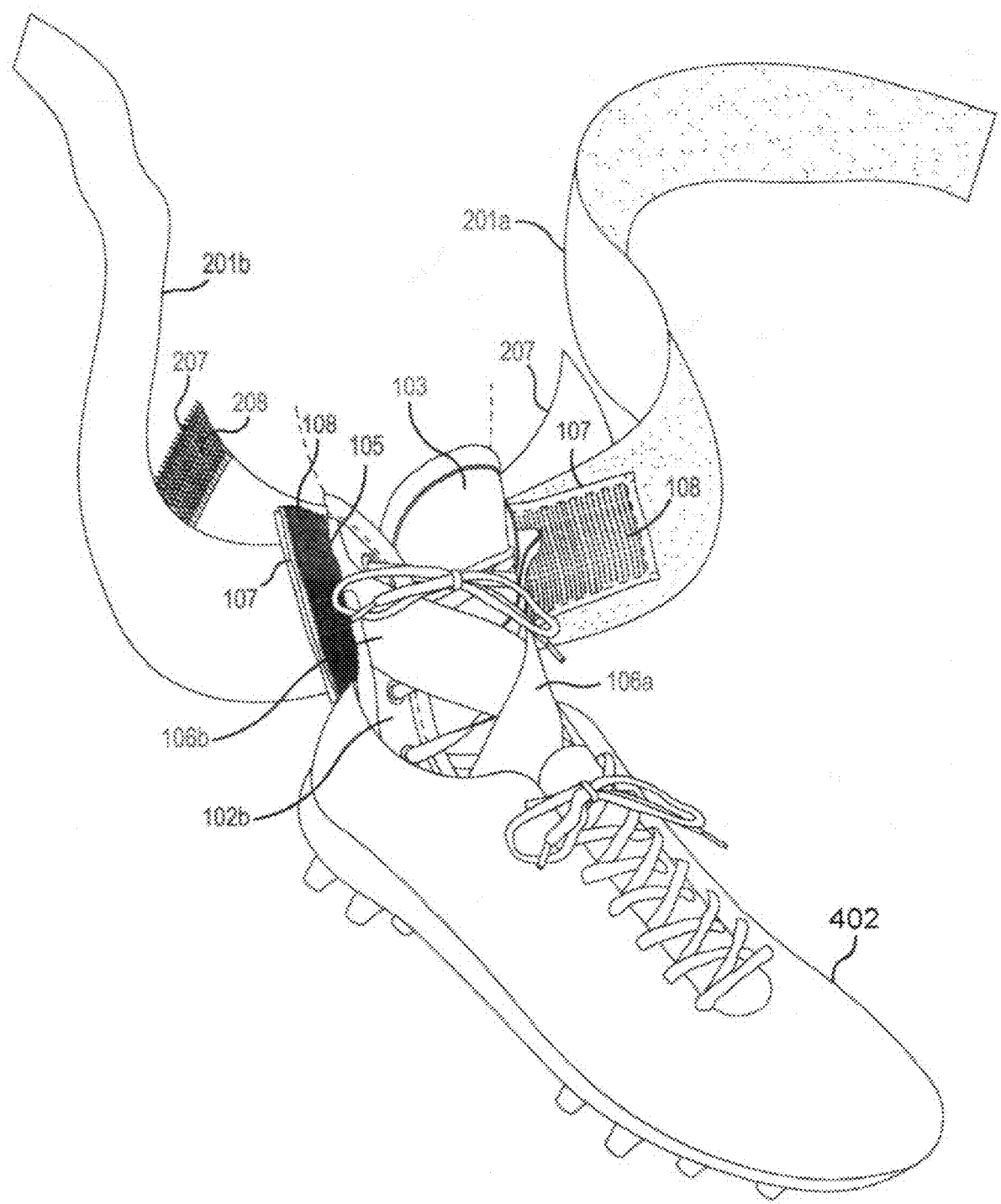
FIG. 4 is a diagram illustrating one embodiment of an ankle brace with the first support strap in place, the first support cuff ready to place, and the second support strap and the second support cuff ready to place.

FIG. 4 illustrates an exemplary embodiment of the ankle brace 200, illustrating first support strap 106 in place, first support cuff 107 ready to place, second support strap 201, and second support cuff 207 ready to place. In FIG. 4, the wearer has inserted the foot 100 wearing the brace 200 into one example of footwear 402. The ankle brace 200 is suitable for use with various types of footwear or shoes 402. The footwear 402 is secured as appropriate around the foot 100 and brace, and first support cuff 107 is secured around the ankle joint either prior to inserting the foot into the footwear or after inserting the foot into the footwear, as will be determined by the footwear itself; however, it is intended that second strap 201 and second support cuff 207 will remain open until the footwear 402 is secure.

FIG. 5 illustrates a close-up view of one embodiment of the ankle brace 200, illustrating the device as utilized with first support strap 106 wrapped around the foot and first support cuff 107 closed around the ankle joint. As also shown in FIG. 5, second support strap 201 and second support cuff 207 remain open at this point in the proper application of the ankle brace 200. In various embodiments, first support cuff 107 includes, on its exterior surface, at least two sections of a releasably affixing material 502, to provide a releasably affixing surface in order to releasably affix the releasably attachable material 801a and 801b on the terminal ends of second support strap 201 on each side of the exterior surface of first support cuff 107. In some embodiments, material 502 may be hook and loop type material.

FIG. 6 illustrates the ankle brace 200 in one exemplary configuration, illustrating first support strap 106 appropriately in place, first support cuff 107 appropriately in place, with second support strap 201 ready to be placed, including opposing end 201a and 201b, and second support cuff 207 ready to be placed. That is, the first support strap 106 and the first support cuff 107 are in their deployed configuration, and the and the second support strap 201 and the second cuff 207 are in their non-deployed configuration. The pocket 102 and first support straps 106a and 106b are inserted in the footwear 402.

Figure 7:
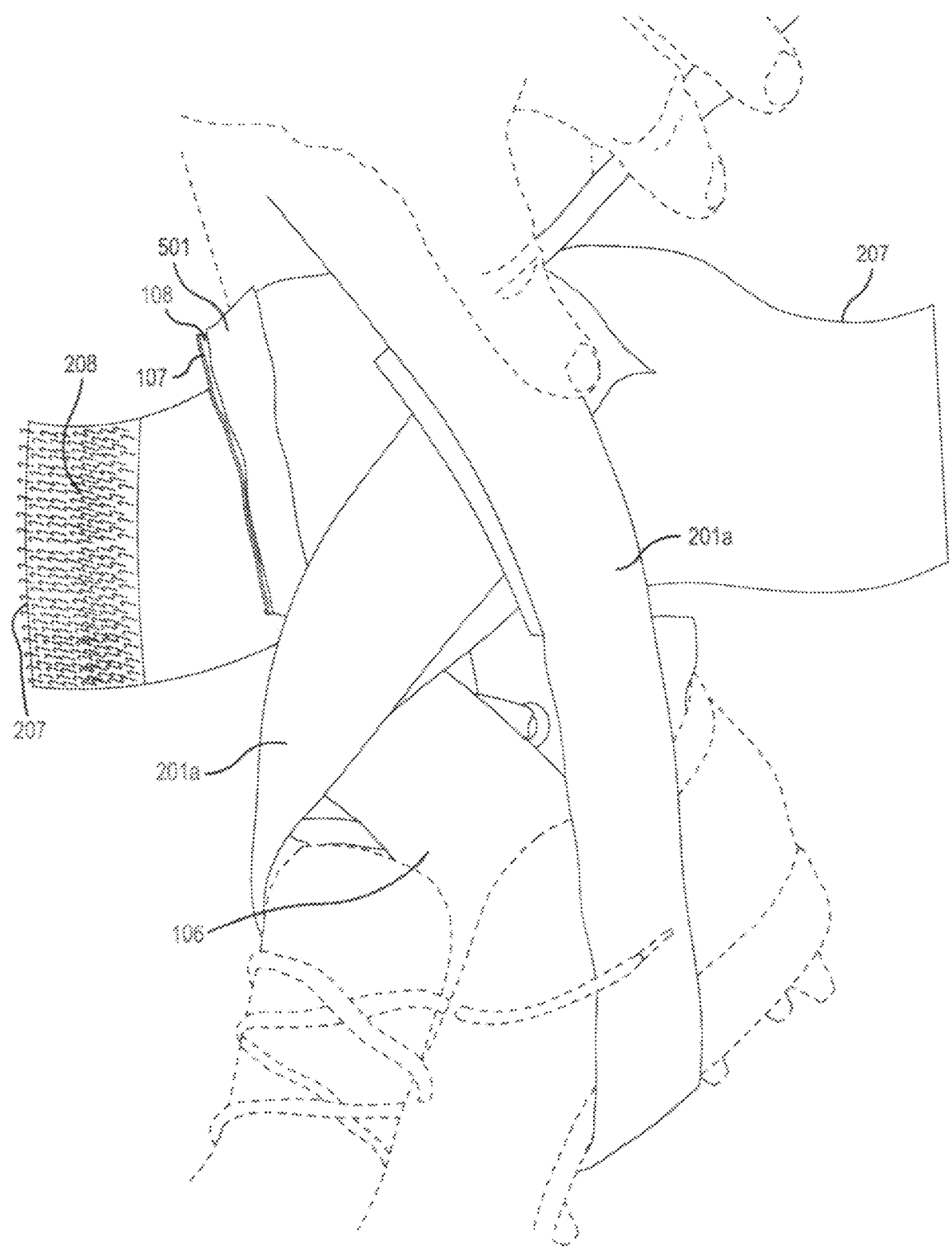
FIG. 7 is a diagram illustrating one embodiment of an ankle brace with the second support strap being put into place and the second support cuff ready to place.

FIG. 7 is a diagram illustrating an example embodiment of the ankle brace 200, illustrating particularly second support strap 201 being put into place. Second support strap 201 has opposing ends 201a and 201b; FIG. 7 illustrates opposing end 201a being secured by wrapping 201a around the exterior of appropriate footwear, beginning around the instep area of the footwear and wrapping forward towards the toe end of the footwear so as to cover the means of closure of the footwear (the means being typically, but not limited to, holes and laces) but avoiding interference with any surface of the sole of the footwear if such surface includes traction-enhancing devices, such as cleats. Once the means of closure of the footwear is covered so as to resemble and imitate "spat tape," wrapping continues of opposing end 201a backwards over itself back towards the foot access portal of the footwear until opposing end 201a is wrapped completely and then can be releasably secured against the exterior surface of first support cuff 107 by releasably attaching surface of cuff 107 or, in another embodiment, by affixing a releasably attaching material to the exterior surface of cuff 107 so as to allow for releasably attaching opposing end 201a against the exterior surface of cuff 107. Similarly, opposing end 201b is secured by wrapping 201b around the exterior of appropriate footwear, axially opposite of 201a's direction of wrapping, so as to cross 201a over 201b at the front of the ankle to provide additional stabilization of the ankle. Opposing end 201b is further wrapped forward towards the toe of the footwear so as to cover the means of closure of the footwear but avoiding interference with any surface of the sole of the footwear if such surface includes traction-enhancing devices, such as cleats. Once the means of closure of the footwear is covered so as to resemble and imitate "spat tape," wrapping continues of opposing end 201b backwards over itself back towards the foot access portal of the footwear until opposing end 201b is wrapped completely and then can be releasably secured against the exterior surface of first support cuff 107 by means of the releasably attaching surface of cuff 107 or, in another embodiment, by affixing a releasably attaching material to the exterior surface of cuff 107 so as to allow for releasably attaching opposing end 201b against the exterior surface of cuff 107.

Figure 8:
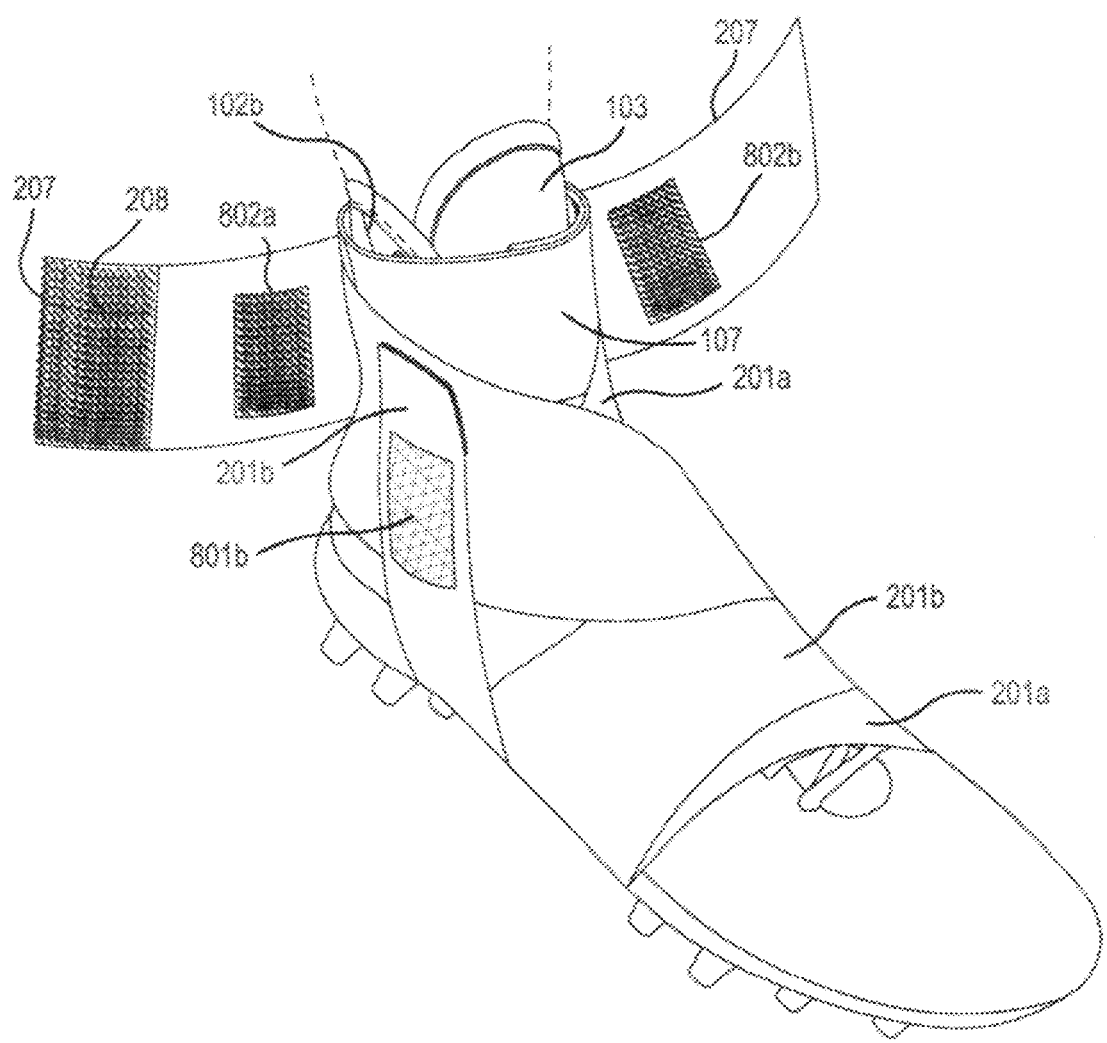
FIG. 8 is a diagram illustrating one embodiment of an ankle brace with the second support strap in place and the second support cuff ready to place.

FIG. 8 is a diagram illustrating an example embodiment of the ankle brace 200, illustrating the present general inventive concept almost completely in place and ready for use. Note particularly second support strap 201 is in place on the exterior of the footwear so as to resemble spat tape. First support cuff 107 is partially visible, having been partially covered by the cross-over wrapping process of 201a and 201b and opposing ends 201a and 201b are releasably attached to their respective selves. (See FIG. 7 description, supra.) Second support strap ends 201a and 201b have sufficient length so as to terminate underneath the lower edge of second support cuff 207 (once closed) and be further secured by releasable means to the exterior of first support cuff 107, with releasably attachable material 801a and 801b on the interior surface of the terminal end of 201a and 201b, respectively, adjacent the pull tabs 225a and 225b, and releasably attachable material 802a and 802b on the exterior surface of the second support strap 201a and 201b. Second support cuff 207 is releasably attached unto itself and secured around the ankle joint by means of releasably attachable material on the interior of one side of cuff 207 (see, for one example, hook material 208) releasably attaching to a releasably attachable material on the exterior of the other side of cuff 207, such as, for one example, loop material (not shown).

FIG. 9 illustrates the ankle brace 200 when fully in place and ready for use. That is, the pocket 102, the straps 106, 201 and the cuffs 107, 207 are in their deployed configuration. Note the overwrapping of ends 201a and 201b to resemble spat tape on the exterior of the footwear. Note also, in this exemplary embodiment, end 201b terminates so as to be under second support cuff 207 when cuff 207 is closed; similarly, although not illustrated herein, end 201a terminates so as to be under second support cuff 207 when cuff 207 is closed.

FIG. 10 illustrates the ankle brace 200 when fully in place and ready for use. Note in this exemplary embodiment, second support strap 201 contains indicia 1002, such as a logo, trademark, or name. The first indicia 1002 is positioned on the second cuff 207 such that the first indicia 1002 is visible with the cuff 207 in its deployed configuration. This is illustrative of one embodiment of the ankle brace 200, but is not intended to be an exhaustive example of such logo or image 1002 that could be placed thereon second support strap 201.

FIG. 11 illustrates the ankle brace 200 when fully in place and ready for use. Note in this exemplary embodiment, second support strap 201 contains second indicia 1002', such as a logo image, specifically in this embodiment, a multi-print logo. The second indicia 1002' is positioned on the second strap 201 such that the second indicia 1002' is visible with the second strap 201 and the second cuff 207 in their deployed configuration. This is illustrative of one exemplary embodiment of the present general inventive concept, but is not intended to be an exhaustive example of such multi-print logo or images 1002' that could be placed thereon second support strap 201.

Figure 12:
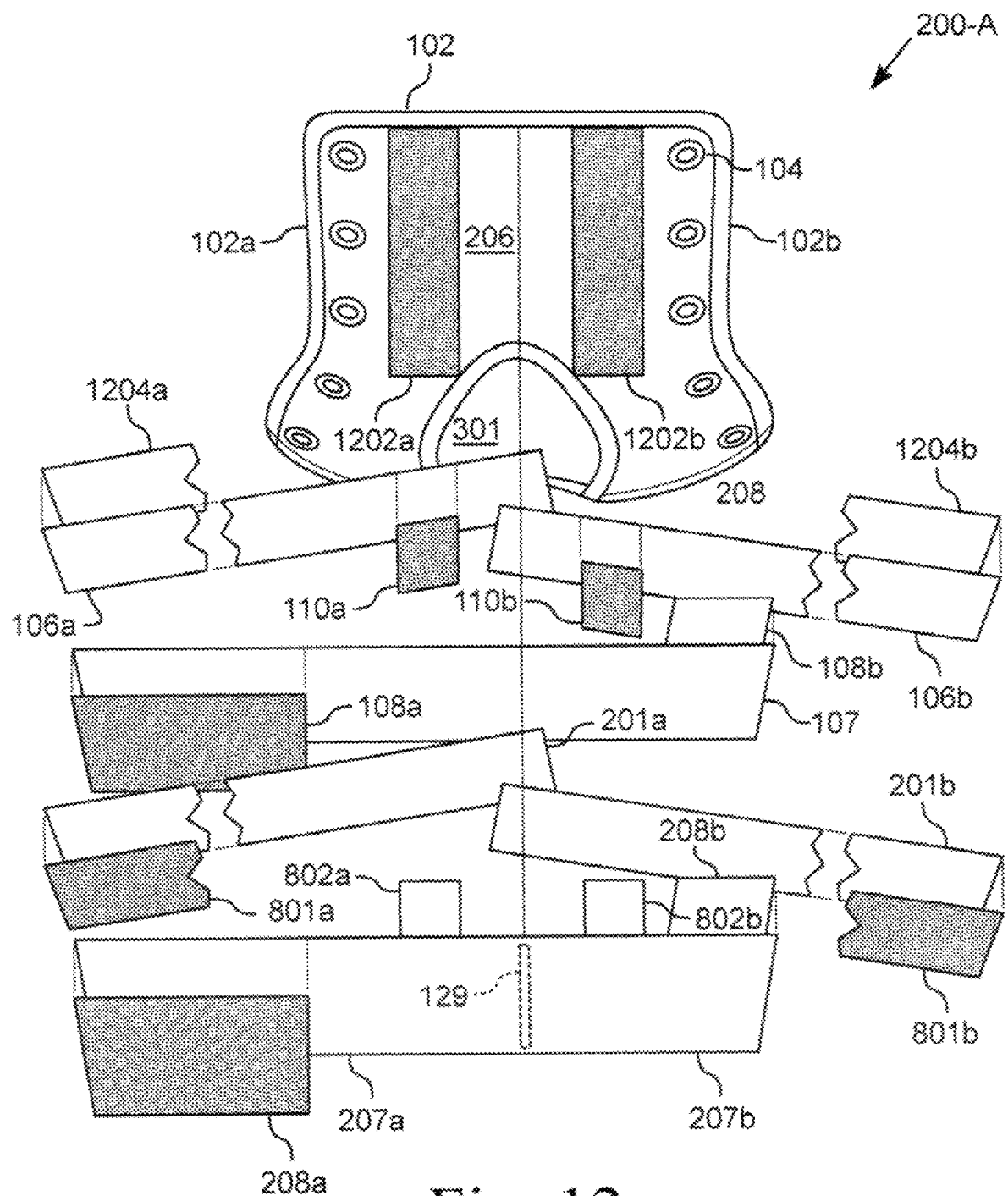
FIG. 12 is an exploded view of one embodiment of an ankle brace.

FIG. 12 illustrates an exploded view of one embodiment of an ankle brace 200-A. The illustrated embodiment of the ankle brace 200-A shows the pocket 102 with a pair of first support straps 106a, 106b, a first support cuff 107, a pair of second support straps 201a, 201b, and a second support cuff 207. In one embodiment, the first support straps 106a, 106b and the second support straps 201a, 201b are non-elastic material and the first support cuff 107 and the second support cuff 207 are elastic material.

A rear view of the pocket 102 is shown with the lace 105 omitted, that is, the lace 105 is not shown engaging the eyes 104. The pocket 102 is spread open, showing the left side 102a and the right side 102b of the pocket 102. The back 206 of the pocket 102 is centered between the two sides 102a, 102b and above the heel opening 301. Adjacent the eyes 104 and between the center of the back 206 and the eyes 104 on each side 102a, 102b is a side connector 1202a, 1202b. The side connectors 1202a, 1202b are positioned to extend down the sides 102a, 102b of the pocket 102, and the sides of the foot 100 when the pocket 102 is worn. In one embodiment the side connectors 1202a, 1202b are one half of a hook and loop connector. In another embodiment, the side connectors 1202a, 1202b are omitted and the ends of the first support straps 106a, 106b attach to the associated strap connectors 110a, 110b.

The first support strap 106 is shown in two pieces 106a, 106b. The two first support straps 106a, 106b overlap where they are attached to the back 206 of the pocket 102. The first straps 106a, 106b are angled downward as they extend away from the back 206 of the pocket 102. Attached to the rear surface of each strap 106a, 106b is a strap connector 110a, 110b that is the same material as the side connectors 1202a, 1202b. The strap connectors 110a, 110b are positioned on the straps 106a, 106b such that the strap connectors 110a, 110b align with the side connectors 1202a, 1202b when the first support straps 106a, 106b are wrapped around the pocket 102.

The ends of the first support straps 106a, 106b include connectors 1204a, 1204b attached to the front, or inside, surface of the straps 106a, 106b. In one embodiment, the connectors 1204a, 1204b are one half of a hook and loop closure material that mates with the side connectors 1202a, 1202b and/or the strap connectors 110a, 110b when the first support straps 106a, 106b are wrapped around the pocket 102 in the deployed configuration.

The first cuff 107 is outboard of the first support straps 106a, 106b. Two halves 108a, 108b of a hook and loop closure material are attached to opposite sides of the first cuff 107 at opposing distal ends. In this way the two halves 108a, 108b mate when the first cuff 107 is wrapped around the ankle 116, the pocket 102, and the wrapped first support straps 106a, 106b. In the illustrated embodiment, the cuff 107 is not centered where attached to the back 206, but is offset such that a double thickness of the first cuff 107 formed where the two ends of the cuff 107 releasably attach is positioned at the side of the ankle 116.

The second support strap 201 is shown in two pieces 201a, 201b. The two second support straps 201a, 201b overlap where they are attached to the first cuff 107 at the back 206 of the pocket 102. The second support straps 201a, 201b are angled downward as they extend away from the back 206 of the pocket 102. Attached to the outboard or outside surface at the distal ends of the second support straps 201a, 201b are releasably attachable material 801a', 801b' that are positioned to mate with the releasably attachable material 802a', 802b' on the inside surface of the second support cuff 207 when the second support straps 201a, 201b are wrapped around the shoe 402.

The second support straps 201a, 201b are two-ply or double-faced material. The inside surface or face is tacky or non-slip and the outside surface is wear resistant. In this way the straps 201a, 201b, when in the deployed position wrapped around the footwear or shoe 402, remain in position relative to the shoe 402 because the inside surface of the straps 201a, 201b grip the outer surface of the shoe 402. Also, the wear resistant feature of the outer surface of the straps 201a, 201b allows for multiple use of the brace 200, 200-A, 200-B as the straps 201a, 201b are exposed to the environment. The second support straps 201a, 201b are the same width or slightly wider than the first support straps 106a, 106b.

The second cuff 207 is outboard of the second support straps 201a, 201b. Two halves 208a, 208b of a hook and loop closure material are attached to opposite sides of the second cuff 207 at opposing distal ends. In this way the two halves 208a, 208b mate when the second cuff 207 is wrapped around the ankle 116, the pocket 102, the wrapped first support straps 106a, 106b, the first cuff 107, and the wrapped second support straps 201a, 201b. In the illustrated embodiment, the cuff 207 is not centered where attached to the back 206, but is offset such that a double thickness of the second cuff 207 formed where the two ends of the cuff 207 releasably attach is positioned at the side of the ankle 116. In one such embodiment, the second cuff 207 has a distal end attached to the back 206 with the cuff 207 wrapping around the ankle 116 and attaching to itself adjacent the seam 129.

The second cuff 207 includes a pair of releasably attachable material 802a', 802b' on the inside surface of the second support cuff 207. The material 802a', 802b' is positioned such that it engages the material 801a', 801b' on the second support straps 201a, 201b when the straps 201a, 201b are wrapped around the shoe 402 and the cuff 207 is wrapped around the ankle 116.

The second cuff 207 is the same width as, or slightly wider than, the first cuff 107. The pocket 102, the two first support straps 106a, 106b, the first cuff 107, the two second support straps 201a, 201b, and the second cuff 207 are secured together with a sewn seam 129.

Figure 13:
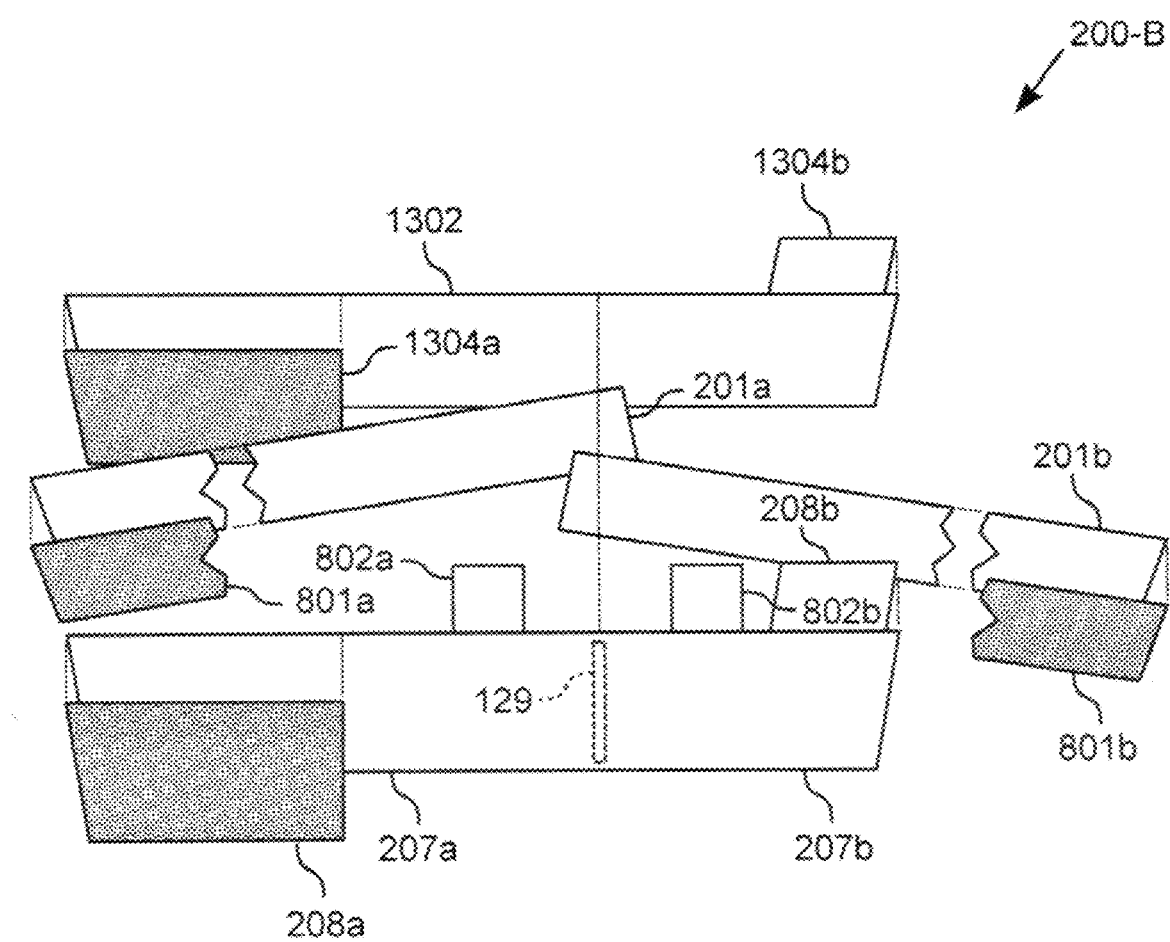
FIG. 13 is an exploded view of another embodiment of the ankle brace.

FIG. 13 illustrates an exploded view of another embodiment of an ankle brace 200-B in which the brace 200-B is configured to be independent of the pocket 102, the first support strap 106, and the first cuff 107. In one embodiment, the brace 200-B is intended to be used in conjunction with an ankle brace with a pocket 102 having a pair of first support straps 106a, 106b and a first support cuff 107. In another embodiment, the brace 200-B is intended to be used without an underlying pocket 102, straps 106, and first cuff 107. In such an embodiment, the brace 200-B is applied to the foot 100 when it is inside a shoe 402.

The illustrated embodiment of the ankle brace 200-B shows an attachment cuff 1302, a pair of second support straps 201a, 201b, and a second support cuff 207. In one embodiment, the second support straps 201a, 201b are non-elastic material and the attachment cuff 1302 and the second support cuff 207 are elastic material.

The attachment cuff 1302 includes two halves 1304a, 1304b of a hook and loop closure material that are attached to opposite sides of the attachment cuff 1302 at opposing distal ends. In this way the two halves 1304a, 1304b mate when the attachment cuff 1302 is wrapped around the ankle 116. The attachment cuff 1302 secures the brace 200-B to the ankle 116 with the second support straps 201a, 201b and the second cuff 207 in a position suitable for the straps 201a, 201b and the second cuff 207 to be deployed to their deployed configuration around the shoe 402 and ankle 116.

The second support straps 201a, 201b overlap where they are attached to the fir attachment cuff 1302. The second support straps 201a, 201b are angled downward as they extend away from the attachment to the attachment cuff 1302. Attached to the outboard or outside surface at the distal ends of the second support straps 201a, 201b are releasably attachable material 801a', 801b' that are positioned to mate with the releasably attachable material 802a', 802b' on the inside surface of the second support cuff 207 when the second support straps 201a, 201b are wrapped around the shoe 402.

The second support straps 201a, 201b are two-ply or double-faced material. The inside surface or face is tacky or non-slip and the outside surface is wear resistant.

The second cuff 207 is outboard of the second support straps 201a, 201b. Two halves 208a, 208b of a hook and loop closure material are attached to opposite sides of the second cuff 207 at opposing distal ends. In this way the two halves 208a, 208b mate when the second cuff 207 is wrapped around the ankle 116, attachment cuff 1302, and the wrapped second support straps 201a, 201b. In the illustrated embodiment, the cuff 207 is not centered where attached to the attachment cuff 1302 and the second support straps 201a, 201b, but is offset such that a double thickness of the second cuff 207 formed where the two ends of the cuff 207 releasably attach is positioned at the side of the ankle 116. In one such embodiment, the second cuff 207 has a distal end secured with a seam 129 with the cuff 207 wrapping around the ankle 116 and attaching to itself adjacent the seam 129.

The second cuff 207 includes a pair of releasably attachable material 802a', 802b' on the inside surface of the second support cuff 207. The material 802a', 802b' is positioned such that it engages the material 801a', 801b' on the second support straps 201a, 201b when the straps 201a, 201b are wrapped around the shoe 402 and the cuff 207 is wrapped around the ankle 116.

The second cuff 207 is the same width as, or slightly wider than, the attachment cuff 1302. The attachment cuff 1302, the two second support straps 201a, 201b, and the second cuff 207 are secured together with a sewn seam 129.

Still other embodiments will become readily apparent to those skilled in this art from reading the above-cited detailed description in view of all the drawings. It is noted that the simplified diagrams do not illustrate all the various connections and assemblies of the various components, however, those skilled in the art will understand how to implement such connections and assemblies, based on the illustrated components, figures, and descriptions provided herein.

While the ankle brace 200, 200-A, 200-B has been illustrated by description of some embodiments, and while the illustrative embodiments have been described in detail, it is not the intention of the applicant to restrict or in any way limit the scope of the appended claims to such detail. Additional modifications will readily appear to those skilled in the art. The invention in its broader aspects is therefore not limited to the specific details, representative apparatus and methods, and illustrative examples shown and described. Accordingly, departures may be made from such details without departing from the spirit or scope of applicant's general inventive concept.

It is also noted that numerous variations, modifications, and additional embodiments are possible, and, accordingly, all such variations, modifications, and embodiments are to be regarded as being within the spirit and scope of the present general inventive concept. For example, regardless of the content of any portion of this application, unless clearly specified to the contrary, there is no requirement for the inclusion in any claim herein or of any application claiming priority hereto of any particular described or illustrated activity or element, any particular sequence of such activities, or any particular interrelationship of such elements. Moreover, any activity can be repeated, any activity can be performed by multiple entities, and/or any element can be duplicated. Accordingly, while the present general inventive concept has been illustrated by description of several embodiments, it is not the intention of the applicant to restrict or in any way limit the scope of the inventive concept to such descriptions and illustrations. Instead, the descriptions, drawings, and claims herein are to be regarded as illustrative in nature, and not as restrictive, and additional embodiments will readily appear to those skilled in the art upon reading the above description and drawings.

What is claimed is:

1. A brace for protective or therapeutic restraint of the ankle or foot, comprising:
   a holding pocket for stabilizing the ankle or foot, said holding pocket being made from flexible material, said holding pocket including a bottom having an interior surface and an exterior surface, a back having an interior surface and an exterior surface, a right side having an interior surface and an exterior surface, and a left side having an interior surface and an exterior surface, said bottom and said back being permanently affixed to said right side and said left side to form said holding pocket;
   means for releasably binding said right side to said left side to secure said holding pocket around said foot and ankle;

a first support strap, said first support strap having two opposing ends, a midpoint, an interior surface and an exterior surface, said interior surface of said first support strap being permanently affixed at said midpoint to said exterior surface of said back of said holding pocket, said first support strap having a first strap length sufficient for each one of said two opposing ends to cross in front of an ankle portion of said holding pocket, extend around a foot portion of said holding pocket, and with said two opposing ends positioned proximate an ankle portion of said holding pocket when said holding pocket is in a deployed configuration wherein said ankle portion is positioned proximate the ankle and a foot portion is positioned proximate the foot;

means for releasably attaching said first support strap;

a first support cuff having two opposing ends, a midpoint, an interior surface and an exterior surface, said interior surface of said first support cuff being permanently affixed at said midpoint to said exterior surface of said first support strap so as to layer said first support cuff onto said first support strap on said back of said holding pocket;

means for releasably attaching said first support cuff to itself, said first support cuff holding captive said two opposing ends of said first support strap;

a second support strap, said second support strap having two opposing ends, a midpoint, an interior surface and an exterior surface, said interior surface of said second support strap being affixed at said midpoint to said exterior surface of said first support cuff, said second support strap having a second support strap length sufficient for each one of said two opposing ends to cross in front of said ankle portion, extending completely around the footwear, and with said two opposing ends positioned proximate said first support cuff when said first support cuff is wrapped around the ankle in said deployed configuration;

means for releasably binding said second support strap;

a second support cuff having two opposing ends, a midpoint, an interior surface and an exterior surface, said interior surface of said second support cuff being affixed at said midpoint to said exterior surface of said second support strap so as to layer said second support cuff onto said second support strap on said back of said holding pocket, said second support cuff having a second cuff width that is at least as wide as a first cuff width of said first support cuff; said second support cuff having a second cuff length sufficient to extend around said ankle when said holding pocket is in said deployed configuration, wherein said second cuff length is sufficient for a first end of said support cuff to engage an opposite end of said second support cuff to secure said second support strap to said ankle portion; and means for releasably attaching said second support cuff to itself.

2. The brace of claim 1, wherein said means for releasably binding said right side to said left side of said holding pocket, and said means for releasably binding said second support strap are complementary.

3. The brace in any one of the preceding claims, further including a space upon said exterior surface of said second support strap for visual presentation of a word or image.

4. The brace of claim 1, wherein said first support strap has a first strap width that is at least as wide as a second strap width of said second support strap, and said second cuff width being greater than said first strap width.

5. The brace of claim 1, wherein each of said two opposing ends of said first support strap includes a first strap pull tab.

6. The brace of claim 1, wherein said first support strap is angled downward away from each side of said back of said ankle portion wherein said first support strap smoothly, without wrinkling or buckling, crosses in front of said ankle portion of said holding pocket when said first support strap is extended around said foot portion, and said second support strap is angled downward away from each side of said back of said ankle portion wherein said second support strap smoothly, without wrinkling or buckling, crosses in front of said ankle portion of said holding pocket when said second support strap is extended around the footwear.

7. A brace for an ankle and foot of a human, comprising:
a holding pocket configured to wrap around the ankle and a portion of the foot when in a deployed configuration, said holding pocket has an ankle portion with a back and a foot portion with a right side and a left side, said holding pocket defined by a flexible sheet-like material, said holding pocket having a deployed configuration wherein said ankle portion is positioned proximate the ankle and said foot portion positioned proximate the foot of the human and said foot is in a footwear;

a first support strap having a right first support strap and a left first support strap, said first support strap attached medially to said back of said ankle portion, said right first support strap being angled downward away from said back of said ankle portion, said left first support strap being angled downward away from said back of said ankle portion, said right first support strap having a right first strap length sufficient to cross in front of said ankle portion, extending around said foot portion, and with a distal portion positioned proximate said ankle portion when said holding pocket is in said deployed configuration, said left first support strap having a left first strap length sufficient to cross in front of the ankle, around said foot portion, and with a distal portion proximate said ankle portion when said holding pocket is in said deployed configuration;

a first cuff attached medially to said back of said ankle portion with said first support strap between said first cuff and said back of said ankle portion, said first cuff having a first cuff length sufficient to extend around the ankle wherein a first end of said first cuff attaches to an opposite end of said first cuff to secure said first support strap to said ankle portion;

a second support strap having a right second support strap and a left second support strap, said second support strap attached medially to said back of said ankle portion, said second support strap being angled downward away from said back of said ankle portion, said left second support strap being angled downward away from said back of said ankle portion, said right second support strap having a right second strap length sufficient to cross in front of said ankle portion, extending completely around the footwear, and with a distal portion positioned proximate said ankle portion when said holding pocket is in said deployed configuration, said left second support strap having a length sufficient to cross in front of ankle, around the footwear, and with a distal portion proximate said ankle portion when said holding pocket is in said deployed configuration; and a second cuff attached to said back of said ankle portion with said first support strap and said first cuff between said second cuff and said back of said ankle portion, said second cuff having a second cuff length sufficient to extend around said ankle wherein a first end of said second cuff attaches to an opposite end of said second cuff to secure said second support strap to said ankle portion.

8. The brace of claim 7 further including a first hook-and-loop fastening system disposed on said first cuff whereby said first end of said first cuff attaches to said opposite end of said first cuff; and a second hook-and-loop fastening system disposed on said second cuff whereby said first end of said second cuff attaches to said opposite end of said second cuff.

9. The brace of claim 7 further including a lace engaging a plurality of holes in said holding pocket, said plurality of holes disposed in a spaced apart, opposed relationship on opposing distal edges of said right side and said left side whereby said holding pocket is secured to the foot when said holding pocket is in said deployed configuration.

10. The brace of claim 7 further including a hook-and-loop fastening system disposed on said first support strap whereby said right first support strap engages said hook-and-loop fastening system when said holding pocket is in said deployed configuration and said right first support strap is deployed to cross in front of said ankle portion, extending around said foot portion, and with said distal portion of said left first support strap positioned proximate said ankle portion and said left first support strap engages said hook-and-loop fastening system when said left first support strap is deployed to cross in front of said ankle portion, extending around said foot portion, and with said distal portion of said left first support strap positioned proximate said ankle portion.

11. The brace of claim 7 further including a first hook-and-loop fastening system disposed on said right first support strap and said ankle portion of said holding pocket whereby when said holding pocket is in said deployed configuration and said right first support strap is deployed to cross in front of said ankle portion, extend around said foot portion, and with said distal portion of said left first support strap positioned proximate said ankle portion, said distal portion of said left first support strap is secured to said ankle portion by way of said first hook-and-loop fastening system, and further including a second hook-and-loop fastening system disposed on said left first support strap and said ankle portion of said holding pocket whereby when said holding pocket is in said deployed configuration and said left first support strap is deployed to cross in front of said ankle portion, extend around said foot portion, and with said distal portion of said left first support strap positioned proximate said ankle portion, said distal portion of said left first support strap is secured to said ankle portion by way of said second hook-and-loop fastening system.

12. The brace of claim 7 further including a hook-and-loop fastening system disposed on said second support strap and said second cuff whereby said right second support strap engages said hook-and-loop fastening system when said holding pocket is in said deployed configuration and said right second support strap is deployed to cross in front of said ankle portion, extending around said foot portion, and with said distal portion of said left second support strap positioned proximate said ankle portion and said left second support strap engages said hook-and-loop fastening system when said left second support strap is deployed to cross in front of said ankle portion, extending around said foot portion, and with said distal portion of said left second support strap positioned proximate said ankle portion.

13. The brace of claim 7 wherein said first cuff and said second cuff each have a cuff width that are substantially equal in size, and wherein said first support strap and said second support strap each have a strap width that are substantially equal in size.

14. The brace of claim 7 wherein said first support strap has a first strap width that is at least as wide as a second strap width of said second support strap, said second cuff having a second cuff width that is at least as wide as a first cuff width of said first cuff, and said first cuff width being greater than said first strap width.

15. The brace of claim 7 wherein each one of said distal portions of said first support strap includes a first strap pull tab, each one of said first strap pull tabs being a loop of material configured for grasping and pulling said first support strap.

16. The brace of claim 7 further including a space upon an exterior surface of said second support strap upon which an indicia is positioned.

* * * * *